United States Patent [19]

Carey

[11] Patent Number: 4,885,687

[45] Date of Patent: Dec. 5, 1989

[54] TRACKIG INSTRUMENTATION FOR MEASURING HUMAN MOTOR CONTROL

[75] Inventor: James R. Carey, St. Paul, Minn.

[73] Assignee: Regents of the University of Minnesota, Minneapolis, Minn.

[21] Appl. No.: 257,194

[22] Filed: Oct. 13, 1988

Related U.S. Application Data

[63] Continuation of Ser. No. 861,052, May 8, 1986, abandoned.

[51] Int. Cl.$^4$ ............................................. A61B 5/10
[52] U.S. Cl. ............................... 364/413.02; 128/774; 128/782; 434/258
[58] Field of Search ............................ 128/774, 782; 364/413.02; 434/163, 258, 261

[56] References Cited

U.S. PATENT DOCUMENTS

| | | | |
|---|---|---|---|
| 3,046,676 | 7/1962 | Hermann | 273/148 X |
| 3,680,545 | 8/1972 | Miller | 128/782 |
| 3,690,020 | 9/1972 | McBratnie | 434/163 |
| 4,325,697 | 4/1982 | Regan | 434/258 |
| 4,349,708 | 9/1982 | Asher | 273/148 X |
| 4,558,864 | 12/1985 | Medwedeff | 273/148 |

FOREIGN PATENT DOCUMENTS 3048296  7/1982  Fed. Rep. of Germany ...... 128/774

OTHER PUBLICATIONS

Excerpt from E. C. Poulton, *Tracking Skill and Manual Control*, Academic Press, N.Y. (1974), pp. 33-38.
R. Jones & I. Donaldson, *Measurement of Integrated Sensory-Motor Function Following Brain Damage by a Computerized Preview Tracking Task*, 3 Int. Rehab. Med., 71-83 (1981).
W. Koerth, *A Pursuit Apparatus: Eye-Hand Coordination*, 31 Pyscyological Monographs, 288-92 (1922).
C. Kelley, *The Measurement of Tracking Proficiency*, 11 Human Factors, 43-64 (1969).
W. Henderson, W. Tourtelloute & A. Potvin, *Training Examiners to Administer a Quantitative Neurological Examination for a MultiCenter Clinical Trail*, 56, Arch. Phys. Med. Rehabil., 289-95 (1975).
K. Cross, *Role of Practice in Perceptual-Motor Learning*, 46 A.N.J. Phys. Med., 487-510 (1967).
R. Eason & C. White, *Relationship Between Muscular Tension and Performance During Rotary Pursuit*, 10 Percept. Mot. Skills, 199-210 (1969).
C. Frith, *Learning Rythmic Hand Movements*, 25, Q. J. Exp. Psych., 253-259 (1973).
M. Abrams & J. Grice, *Effects of Practice in Positional Variables and Acquisition of a Complex Psychomotor Skill*, 43, Percept. Mot. Skills, 203-211 (1976).

(List continued on next page.)

Primary Examiner—Jerry Smith
Assistant Examiner—Kibby, Steven
Attorney, Agent, or Firm—Merchant, Gould, Smith, Edell, Welter & Schmidt

[57] ABSTRACT

Tracking instrumentation for measuring human motor control includes a load cell or potentiometer for converting a force or position to an electrical signal. An analog-to-digital converter periodically samples the electrical signal and converts it into a series of digital words representing a force amplitude value. A computer system includes a monitor for displaying a tracking element, the position of the tracking element controlled by the digital words. The computer system further includes means for displaying a tracking pattern on the monitor and plotting scaled values on the monitor superimposed on the tracking pattern. The values are plotted so that the user operating a handgrip can adjust the handgrip in an attempt to track the pattern across the monitor. The system further includes means and methods for recording and analyzing the tracking performance data and for objectively scoring the tracking data.

7 Claims, 10 Drawing Sheets

OTHER PUBLICATIONS

S. Hagan, H. Wilkerson & C. Noble, *Pursuit Tracking Skill as a Joint Function of Work and Rest Variables,* 50, Percept. Mot. Skills, 683–697 (1980).

K. Flowers, *Some Frequency Response Characteristics of Parkinsonism on Pursuit Tracking,* 101, Brain, 19–34 (1978).

H. Beppu, M. Suda & R. Tanaka, *Slow Visuomotor Tracking in Normal Man and in Patients with Cerebellar Ataxia,* 39 Advances in Neurology, 889–895 (1983).

H. Beppu, M. Suda & R. Tanaka, *Analysis of Cerebellar Motor Disorders by Visually Guided Elbow Tracking Movement,* 107, Brain, 787–809 (1984).

A. Potvin & W. Tourtellotte, *The Neurological Examination: Advancements in Its Quantification,* 56, Arch. Phys. Med. Rehabil, 425–437 (1975).

L. DeSouza, R. Hewer, P. Len, S. Miller and G. Reid, *Assessment of Recovery of Arm Control and Hemiplegic Stroke Patients: Comparison of Arm Function Test and Pursuit Tracking in Relation to Clinical Recovery,* 2, Int. Rehab. Med., 10–16 (1980).

L. Carlton, *Movement Control Characteristics of Aiming Responses,* 23, Ergonomics, 1019–1032 (1980).

FIG. I
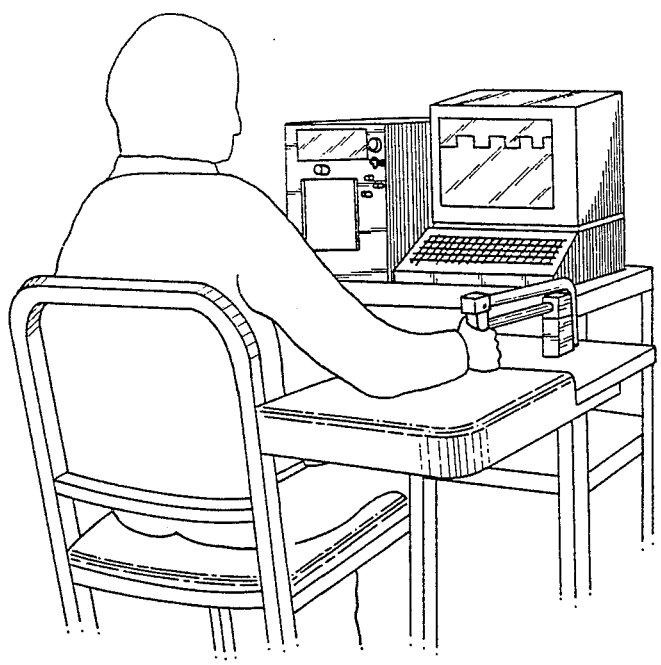
FIG. 4
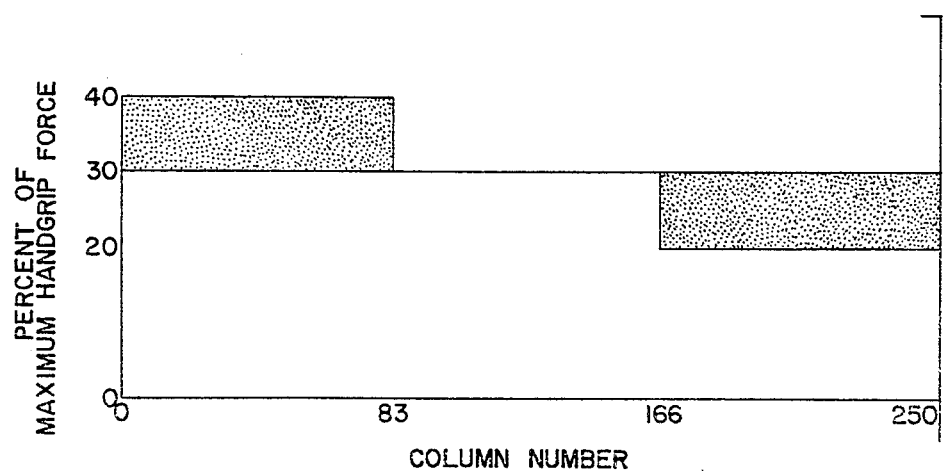

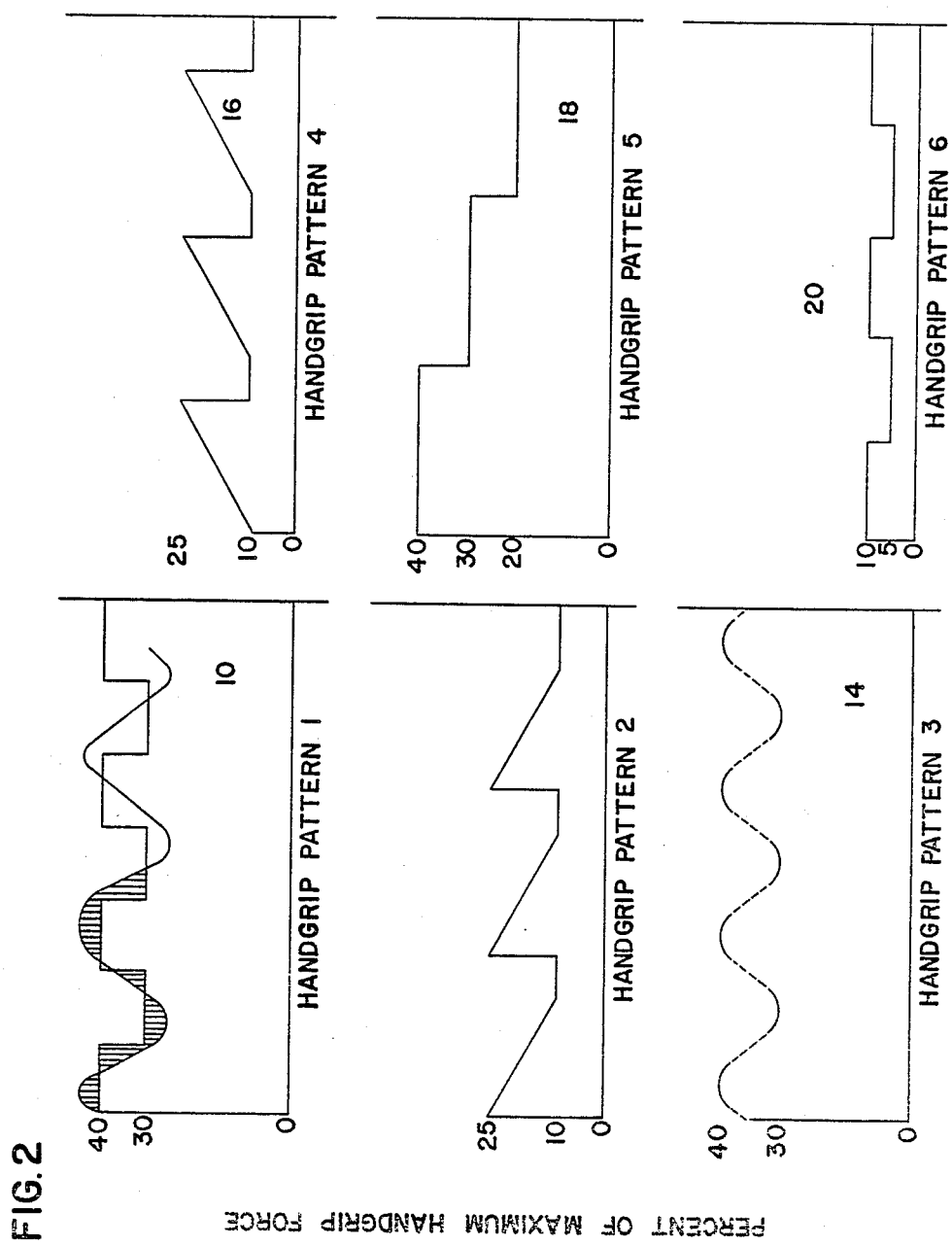

FLOW CHART FOR TRACKING JOINT POSITION

TRACKIG INSTRUMENTATION FOR MEASURING HUMAN MOTOR CONTROL

This is a continuation, of application Ser. No. 861,052 filed May 8, 1986 and now abandoned.

BACKGROUND OF THE INVENTION

One basic element in the control of human movement is the ability to correctly adjust the magnitude and temporality of muscle contractions to meet the requisites of precision-demanding motor tasks. Tracking experiments have been advocated as an ideal protocol for quantitating such skillful performance. See K. Cross, Role of Practice in Perceptual-Motor Learning, 46 Am. J. Phy. Med. 487-510 (1967); E. Poulton, Tracking Skill and Manual Control, New York, Academic Press, Inc. (1974); R. Jones & I. Donaldson, Measurement of Integrated Sensory-Motor Function Following Brain Damage By a Computerized Preview Tracking Task, 3 Int. Rehab. Med. 71-83 (1981); A. Potvin & W. Tourtellotte, Quantitive Examination of Neurological Functions, Vols. 1-2, Boca Raton, FL, CRC Press, Inc. (1985).

Tracking is the effort to accurately pursue some desired target by careful adjustment of the intensity and timing of muscle contractions, and is guided by the surveillance of one or more sensory cues. The desired target may be a certain force level, joint angle, eye position or the precise placement of an object in space. Common examples of tracking in daily living include: accurately reaching for an object, visually following a moving object, steering a vehicle, and handwriting. All of these activities involve a closed-loop negative feedback mechanism of control whereby ongoing integration between a faithful sensory system and a responsive motor system is used to minimize the undershoot or overshoot error about the desired target.

Measurement of tracking performance as an indicator of motor control has been documented as early as 1922. See W. Koerth, A Pursuit Apparatus: Eye-Hand Coordination, 31 Psychological Monographs 288-92 (1922). A particular surge of interest in this topic occurred during and immediately after World War II with a focus on gunnery skills. See C. Kelley, The Measurement of Tracking Proficiency, 11 Human Factors 43-64 (1969). Psychologists and educators have utilized tracking tests as a method of elucidating some of the intricacies of motor-control learning. See R. Eason & C. White, Relationship Between Muscular Tension and Performance During Rotary Pursuit, 10 Percept. Mot. Skills 199-210 (1969); C. Frith, Learning Rhythmic Hand Movements, 25 Q. J. Exp. Psych. 253-59 (1973); M. Abrams & J. Grice, Effects of Practice and Positional Variables in Acquisition of Complex Psychomotor Skill, 43 Percept. Mot. Skills 203-11 (1976); S. Hogan, H. Wilkerson & C. Noble, Pursuit Tracking Skill as a Joint Function of Work and Rest Variables, 50 Percept. Mot. Skills 683-97 (1980). Medical science has employed tracking experimentation as a means of documenting motor control in individuals with such neuromuscular conditions as Parkinson's disease, see K. Flowers, Visual "Closed-Loop" and "Open-Loop" Characteristics of Voluntary Movement in Patients with Parkinsonism and Intention Tremor, 99 Brain 269-310 (1976); K. Flowers, Some Frequency Response Characteristics of Parkinsonism on Pursuit Tracking, 101 Brain 19-34 (1978), cerebella ataxia, see H. Beppu, M. Suda & R. Tanaka, Slow Visuomotor Tracking in Normal Man and in Patients with Cerebellar Ataxis, 39 Advances in Neurology 889-95 (1983); H. Beppu, M. Suda & R. Tanaka, Analysis of Cerebellar Motor Disorders of Visually Guided Elbow Tracking Movement, 107 Brain 787-809 (1984), multiple sclerosis, see W. Henderson, W. Tourtelloute & A. Potvin, Training Examiners to Administer A Quantitative Neurological Examination for a Multicenter Clinical Trial, 56 Arch. Phys. Med. Rehabil. 289-95 (1975); A. Potvin & W. Tourtellotte, The Neurological Examination: Advancements in its Quantification, 56 Arch. Phys. Med. Rehabil. 425-37 (1975), and head trauma, see R. Jones & I. Donaldson, Measurement of Integrated Sensory-Motor Function Following Brain Damage By a Computerized Preview Tracking Task, 3 Int. Rehab. Med. 71-83 (1981); L. DeSouza, R. Hewer, P. Lynn, S. Miller & G. Reed, Assessment of Recovery of Arm Control in Hemiplegic Stroke Patients: Comparison of Arm Function Tests and Pursuit Tracking in Relation to Clinical Recovery 2 Int. Rehab. Med. 10-16 (1980).

These contributions to the concern of motor control in humans are commendable; however, the fruits of these valuable efforts have not been fully exploited in rehabilitation. Heretofore procedures of measuring motor control have included such tests as reaction time, movement time, reciprocal tapping, and peg transfer. See L. Carlton, Movement Control Characteristics of Aiming Responses, 23 Ergonomics 1019-32 (1980); R. Schmidt, Motor Control and Learning, Champaign, Human Kinetics Pub. (1982). While each of these tools does yield information about certain ingredients of motor control, they do not provide the desired objective quantitation of an individual's ability to actuate the precise level and punctuality of muscular activity required by a specific motor task.

There still exists a critical need to quantify the efficacy of various therapeutic procedures purported to improve motor function in disabled individuals. Documentation related to muscular strength certainly abounds in the literature. And although the capacity to exert strong muscular forces is advantageous to an individual, the great preponderance of activities of daily living require, not so much strong efforts, but rather well-controlled efforts typically within the individual's existing force range.

Tracking experiments provide a rigorous and objective method with which to obtain such documentation of motor control. This invention describes a method and instrumentation for quantitating functional motor performance using pursuit tracking scores and determining the sensitivity of this method in detecting improved performance in normal individuals resulting from limited practice at a series of paced tracking tasks.

BRIEF DESCRIPTION OF THE DRAWINGS

FIG. 1 shows a test subject sitting in front of the tracking instrumentation. The monitor is displaying a handgrip pattern;

FIG. 2 shows six handgrip tracking patterns with percentage of maximum handgrip force plotted versus time;

FIG. 4 shows handgrip pattern 5 and an artificial tracking response with maximum handgrip force set at 100 lbs;

DETAILED DESCRIPTION OF THE INVENTION

Figure 8:
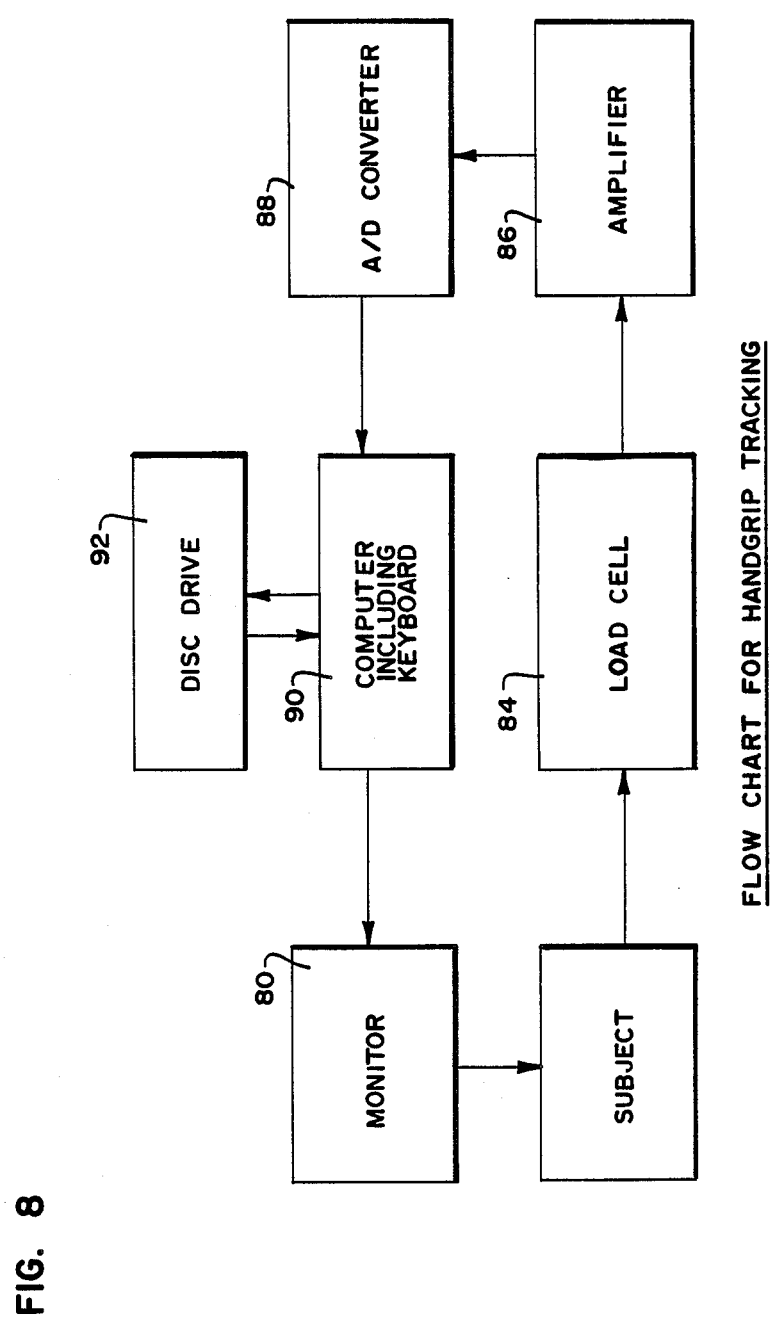
FIG. 8 is a schematic diagram of the system when it is configured for handgrip tracking.

Two tracking maneuvers are used to measure motor control in this invention. FIG. 1 shows a test subject seated in front of the handgrip tracking instrumentation. FIG. 8 is the schematic diagram of this handgrip instrumentation. The control device is handgrip dynamometer 83 connected to load cell 84. Preferably, the load cell is an Interface load cell manufactured by Interface, Inc., 7401 East Butherus Drive, Scottsdale, Arizona 85620, or one of like design. The voltage output of load cell 84 is amplified by amplifier 86. Preferably, the amplifier is a Gould chart recorder manufactured by Gould, Inc., 3631 Perkins Avenue, Cleveland, Ohio 44114, or one of like design. This amplified voltage is input to analog-to-digital converter 88. Preferably, the analog-to-digital converter is an Interactive Model AI 13 manufactured by Interactive Structures, Inc., 146 Montgomery Avenue, Bala Cynwyd, Pennsylvania 10004, or one of like design. The digital output of analog-to-digital converter 88 is input to computer 90. Preferably, the computer is an Apple IIe manufactured by Apple Computer, Inc., 20525 Mariani Avenue, Cupertino, Calif. 95014, or one of like design. Computer 90 displays the result on monitor 80 and also sends the result to disc drive 92 for storage. The preferred embodiment of this system is accurate to within 0.35 pounds over a range of 0 to 300 pounds.

Figure 9:
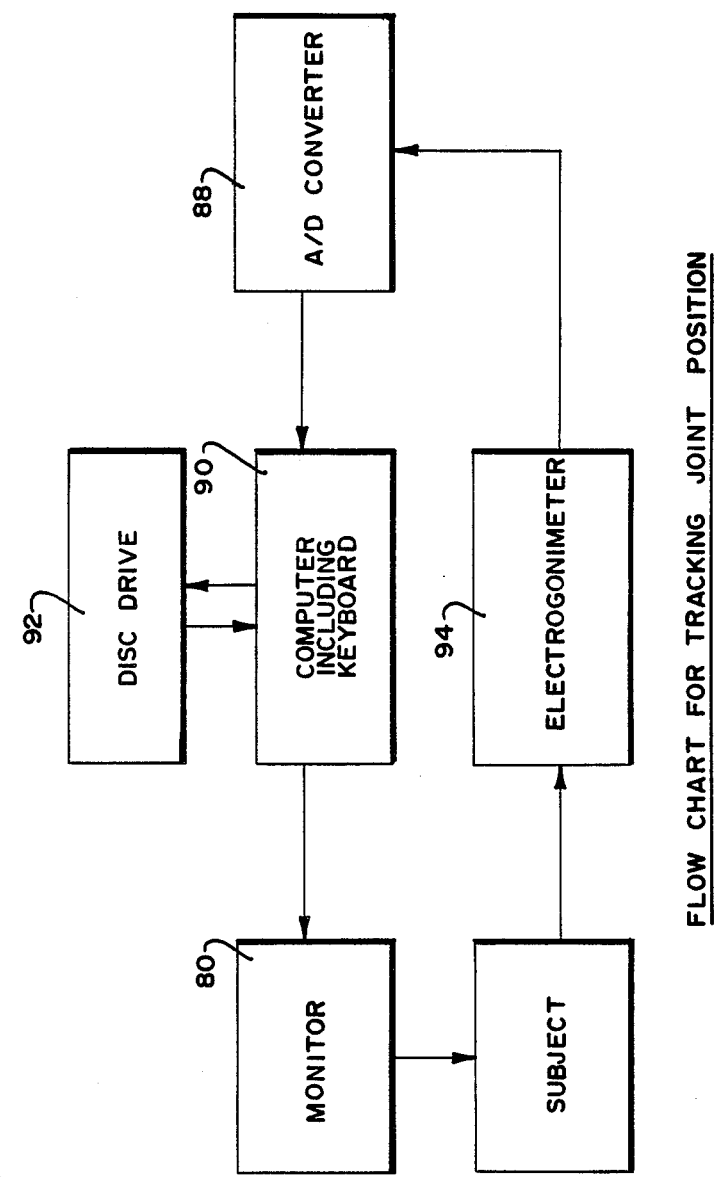
FIG. 9 is a schematic diagram of the system when it is configured for joint-position tracking.

FIG. 9 is the schematic diagram of the instrumentation for the joint-position tracking maneuver. The control device in this instrumentation is electrogonimeter 94. The output of electrogonimeter 94 is input to analog-to-digital converter 88 which outputs a digital signal to computer 90. Computer 90 displays the result on monitor 80 and also sends the result to disc drive 92 for storage. The preferred embodiment of this system is accurate to within 1 degree over a range of 0 to 90 degrees.

Figure 10:
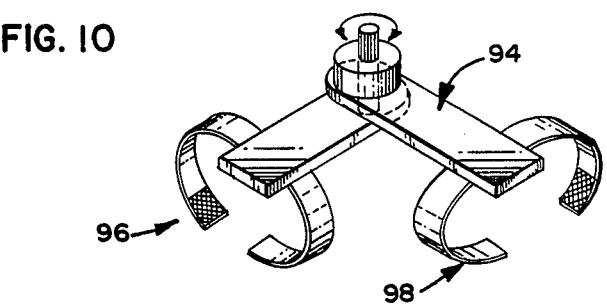
FIG. 10 shows an electrogonimeter for measuring the angle of a joint.
Figure 11:
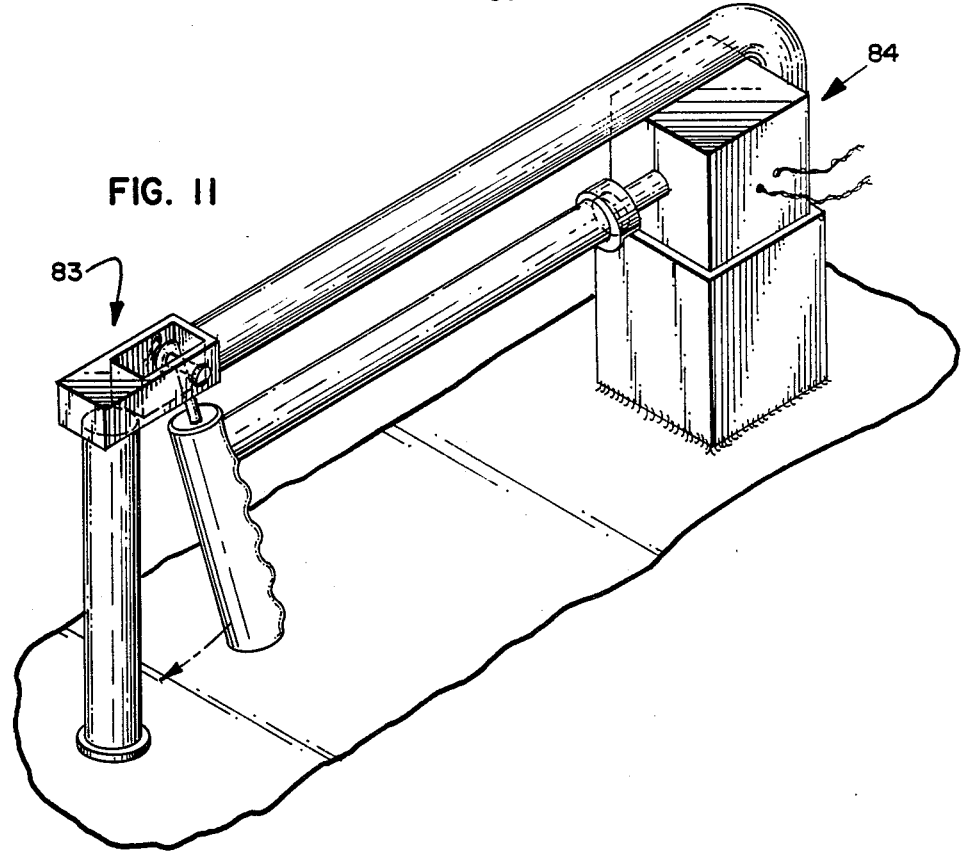
FIG. 11 shows a handgrip dynamometer connected to a load cell.

FIG. 11 shows handgrip dynamometer 83 and load cell 84. When handgrip dynamometer 83 is squeezed, load cell 84 produces a voltage proportional to the force of the squeeze. FIG. 10 shows electrogonimeter 94. Finger grips 96 and 98 are designed to be centered along the radial side of the MP joint of the index finger. When this joint is moved, finger grips 96 and 98 move relative to each other and electrogonimeter 94 produces a voltage proportional to the direction and amount of movement of finger grips 96 and 98.

Figure 12:
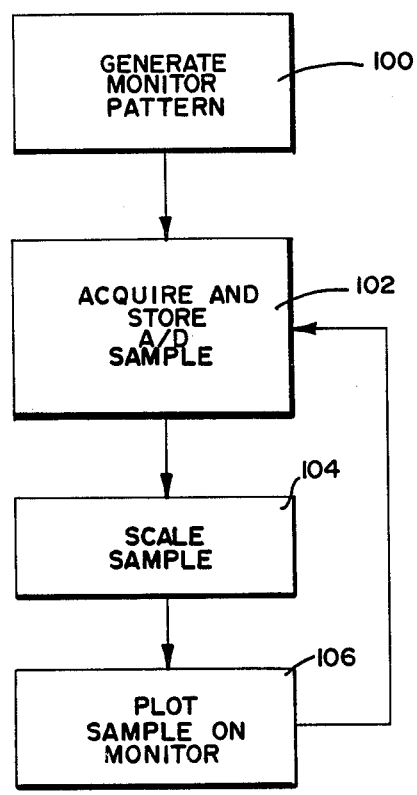
FIG. 12 is a schematic flowchart diagram of the testing software of the present invention.

FIG. 12 is a schematic flow chart of the testing software of this invention. For the handgrip tracking maneuver, Routine 100 generates and displays on monitor 80 the six handgrip patterns shown in FIG. 2. These handgrip patterns are plots of percent of maximum handgrip force versus time. Routine 100 also displays a cursor on monitor 80 that moves automatically from left to right across each pattern with a sweep speed of 10 seconds. Furthermore, the cursor is capable of moving vertically up or down on monitor 80 in exact response to the applied force at handgrip dynamometer 83. Thus, the task for a subject is to trace the cursor along the target pattern as accurately as possible by skillful adjustment of handgrip force. Routine 100 extricates reaction time from the tracking task by displaying the cursor for 0.2 second before the cursor commences its 10-second sweep across each pattern.

For any given pattern, the height and width dimensions on monitor 80 are the same for all subjects. However, the vertical scale of each pattern is customized to each individual and set as a percentage of that individual's predetermined maximum handgrip force. In this fashion the patterns are standardized among all individuals despite differences in strength.

Figure 3:
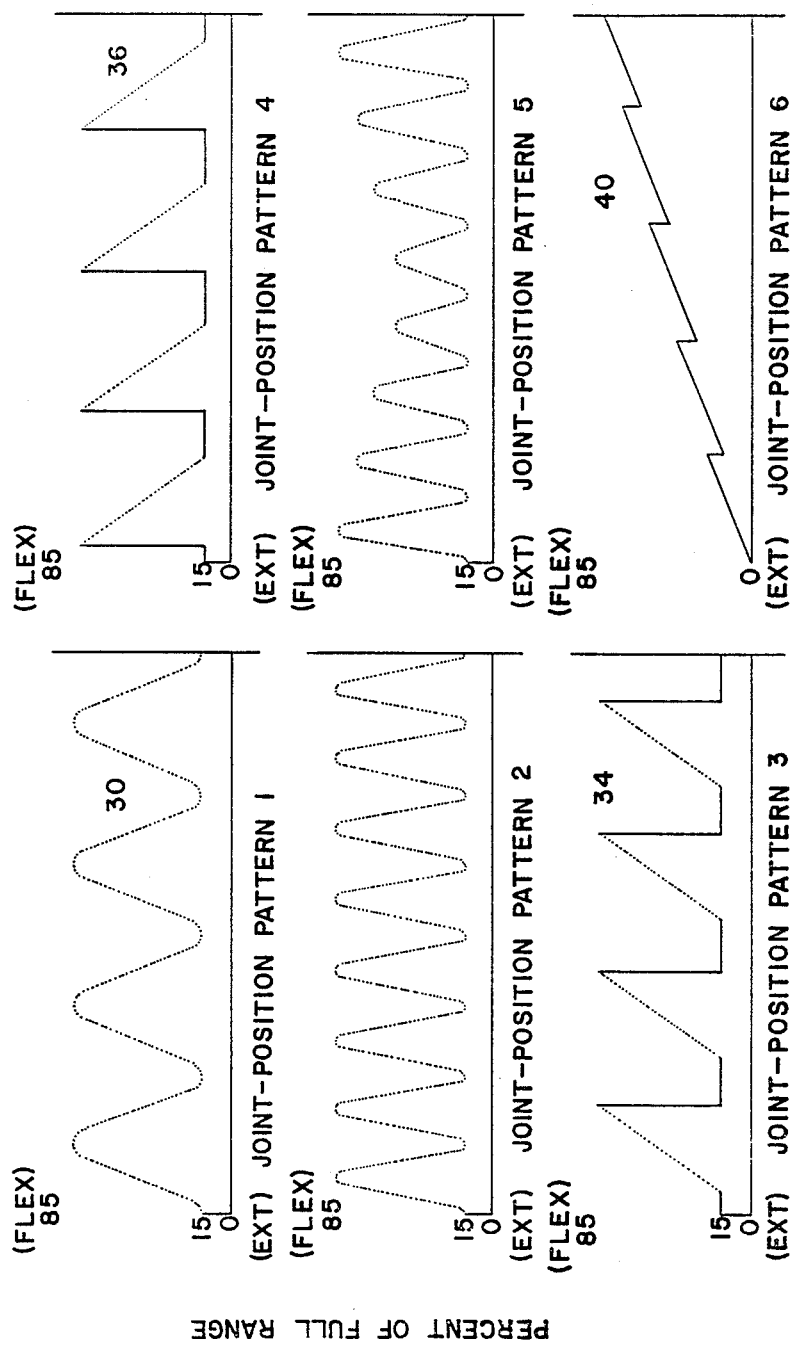
FIG. 3 shows six joint-position tracking patterns with percentage of full range plotted versus time.

Routine 100 also displays a series of target patterns for the joint-position tracking maneuver. The amplitude of these patterns is set as a percentage of an individual's predetermined maximum range of MP flexion-extension at the index finger. FIG. 3 shows the six standardized joint-position patterns with percent of full range plotted versus time. The sweep speed across each pattern is 10 seconds and the objective is to trace the cursor as accurately as possible along the target course by delicate adjustment of the flexion-extension position of the index finger MP joint. The baseline of the pattern is set to be full extension; flexion of the MP joint then moves the cursor up monitor 80 while extension lowers the cursor.

Routine 102 acquires data from analog-to-digital converter 88. Data is sampled at a rate of 100 samples per second. Routine 102 also sends the digital data to disc drive 92 for storage. Routine 104 scales the sampled digital data by using the predetermined maximum handgrip force or maximum range of joint flexion-extension of that individual to determine what percentage of maximum force or range the digital sample is. Routine 106 plots the scaled sample on monitor 80 superimposed on the pattern that the individual is attempting to trace. The sample is plotted in real time so that the individual tracing the pattern can adjust the force or joint position in an attempt to track the pattern.

Each individual subject performs a pretest and post-test tracking attempt. In the first part of the handgrip pretest, the maximum handgrip force of the subject is determined. Each individual is seated in a chair with the right forearm supported on an elevating table that is adjusted so that the hand gripping handgrip dynamometer 83 is comfortable. The handgrip is adjusted to form a 110 degree angle at the proximal interphalangeal joint of the middle finger. See M. Mundale, Study of Relationship of Endurance During Isometric Contraction of Muscles of Handgrip, MS Thesis, University of Minnesota (1964). Monitor 80, which displays the tracking patterns, is positioned 70 centimeters in front of the subject.

Each individual exerts three maximal handgrip contractions, separated by one-minute rest periods. The subject is allowed three low-intensity warmup contractions just prior to each maximal effort. Verbal coaching is provided during the maximal efforts. The highest value is used to set the amplitude of the subsequent handgrip tracking patterns for that subject.

The subject is then instructed to trace each of the ensuing six patterns as accurately as possible by squeezing the handgrip with the correct intensity and timing. A two-second rest occurs between each consecutive pattern.

At the end of the first pretest trial of the six handgrip patterns, the computer calculates the error of the response. This error calculation will be explained in more detail below. This computation requires $1\frac{1}{2}$ minutes during which time the subject rests. Two additional trials, with identical rest periods, complete the handgrip pretest, whereupon the joint-position pretest is initiated.

For the joint-position tracking maneuver, electrogoniometer 94 is secured across the radial side of the MP joint of the index finger. The subject's forearm is supported on the table midway between pronation and supination with the elbow flexed to approximately 90 degrees. The wrist position is unrestricted. The maximum available range of MP flexion-extension is then determined and the subsequent tracking patterns set in reference to this range.

The subject is directed to trace the pattern as exactly possible by delicate adjustment of the flexion-extension position of the MP joint. Three scored trials at all six patterns are executed using the same rest periods as before.

There is a 30-minute rest period between the pretest and the post-test during which time the subjects are allowed to casually move about. Execution of the post-test is identical to the pretest procedure including the determination of new maximum values for handgrip force and MP flexion-extension range.

Figure 13:
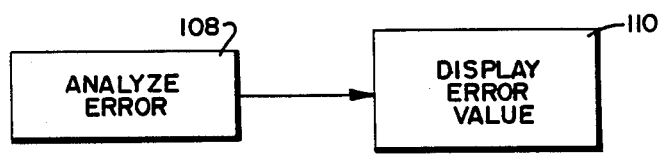
FIG. 13 is a schematic flowchart diagram of the error calculation software of the present invention.

After an individual completes a pretest or a post-test tracking attempt, the error of the performance is calculated. FIG. 13 shows a schematic flowchart diagram of this error calculation. Routine 108 manipulates the data and computes two values of performance for each tracking effort: a root-mean-square (RMS) error score and an accuracy index (AI) score. FIG. 4 shows handgrip tracking pattern 5, shown as 18 on FIG. 2, along with an artificial response used to validate the computer-derived scores. In this example, an electrical signal is used to simulate a maximum handgrip force equivalent to a convenient 100 lbs. Thus, the target force levels for this three-step pattern, as defined in 18 on FIG. 2, are 40, 30 and 20 pounds from left to right. The tracking response to this pattern is fabricated with an electrical signal to be a constant 30 lbs. force for the 10-second tracking period. Routine 108 calculates the RMS error between the pattern and the response according to the formula:

$$RMS \text{ error} = \sqrt{\frac{\sum_{i=1}^{N}(R_i - T_i)^2}{N}}$$

Where
R = actual response
T = desired target
N = number of error measurements

The number of error measurements (N) is fixed by the types of computer 90 and monitor 80 used. In the preferred embodiment, the portion of monitor 80 allocated to the tracking pattern itself is divided into 250 vertical columns by computer 90, which allows for 250 discrete error measurements between the target and the response.

By noting the difference between the target and the response in each of the 250 columns of the pattern in FIG. 4, the RMS error is manually calculated with the above formula to equal 8.173 lbs. This number is exactly equal to the value obtained by routine 108 when confronted with the same data.

The AI is a standardized score that is computed to account for the differences in strength among individuals and, thereby, the differences in the amplitude scale for a given pattern among individuals. This value is calculated as follows:

$$AI = 100(P-E)/P = 100(1-E/P)$$

Where
P = RMS difference between the pattern and the baseline, and
E = RMS error between the target and the response, as calculated previously.

For the example shown in FIG. 4:

$$P = \sqrt{\frac{\sum_{i=1}^{250}(T_i - B)^2}{250}} = 31.055 \text{ lbs.}$$

Where
T = the desired target value
B = baseline value = 0

Therefore, the AI for this example is:

$$AI = 100(1 - 8.173 \text{ lbs}/31.055 \text{ lbs.}) = 73.682\%$$

which is in exact agreement with the value obtained by routine 108.

Routine 110 in FIG. 13 displays the error values obtained by routine 108 on monitor 80.

Figure 5A:
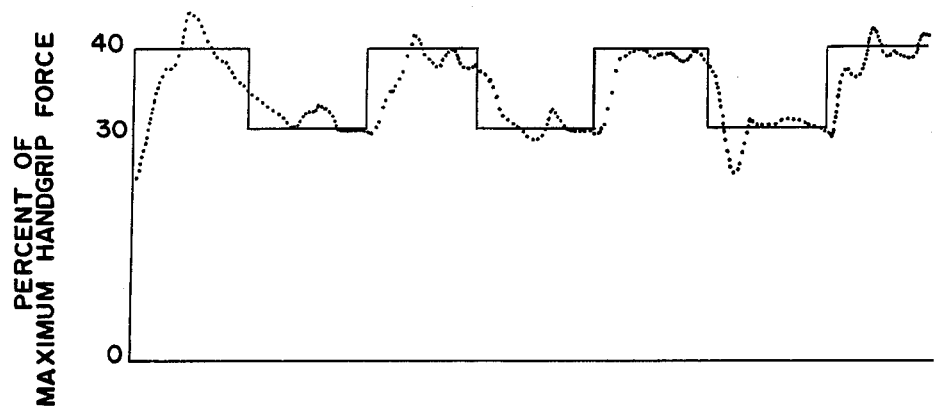
FIG. 5a shows a test subject's pretest handgrip tracking performance for handgrip test pattern 1.
Figure 5B:
FIG. 5b shows a test subject's post-test handgrip tracking performance for handgrip test pattern 1.

The first of the trials of each pretest and posttest tracking series is considered a warmup for all individuals and does not enter into the statistical analysis. The average of the second and third trials of each pretest and post-test tracking effort is considered to be the best indicator of an individual's typical performance. Such averages are computed by routine 108 of FIG. 13 for both RMS error scores as well as for AI scores. The changes in these values from pretest to post-test are analyzed with paired t-tests. The tracking results of ten individuals are summarized in Tables I and II. These 10 volunteers included 8 females and 2 males raning in age from 21–30 years with a mean of 23 years. All are right-handed and no individual had any known hand disfunction, neurological impairments nor interfering visual disturbances. In Tables 1 and 2 accurate tracking performance is represented by high AI scores and low RMS error scores. A typical performance depicting the improvement in tracking skill from pretest to post-test in the handgrip tracking maneuver is seen in FIGS. 5a and b. FIGS. 5a and 5b show handgrip pattern 1, shown as 10 in FIG. 2, as a solid line. The subject's tracking performance is shown as a dotted line in FIGS. 5a and 5b. FIG. 5a is the pretest performance plot and FIG. 5b is the post-test performance plot. RMS and AI for FIG. 5a are 3.429 lbs. and 88.703% respectively while RMS and AI for FIG. 5b are 2.87 lbs. and 90.359% respectively. This improvement can be seen visually by comparison of FIGS. 5a and 5b.

Figure 6A:
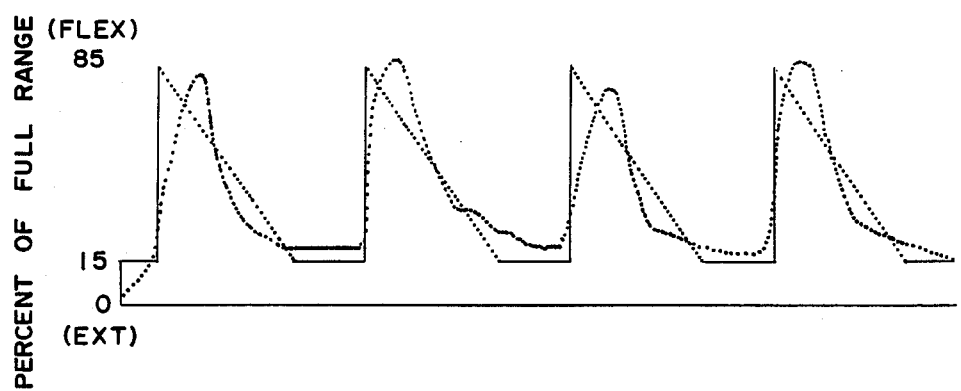
FIG. 6a shows a test subject's pretest joint-position tracking performance for joint-position pattern 4.
Figure 6B:
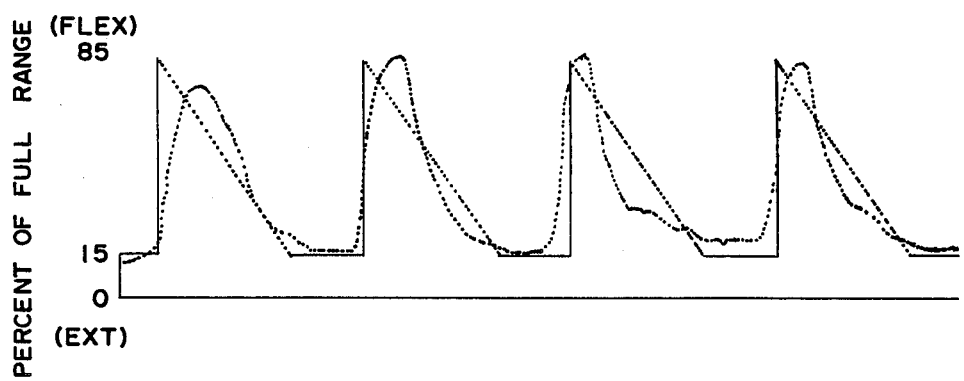
FIG. 6b shows a test subject's post-test joint-position tracking performance for joint-position pattern 4.

Similarly, the improvement in tracking skill from pretest to post-test in the joint-position maneuver is shown in FIGS. 6a and 6b. These two tracking performances show joint-position pattern 4, shown as 36 in FIG. 3, as a solid line and the subject's tracking performance is shown as a dotted line. FIG. 6a and 6b are the pretest and post-test performance respectively. RMS and AI for FIG. 6a are 3.228° and 76.517% respectively while RMS and AI for FIG. 6b are 2.66° and 82.33% respectively. Again, the improvement can be seen visually by comparison of FIGS. 6a and 6b.

Table I shows that there is a consistent sensitivity between the RMS and AI measures in detecting change in handgrip tracking performance. Both scoring methods show statistically significant improvement in patterns: 2($p<0.05$), 4($p<0.001$) and 6($p<0.01$)

Table I also suggests that handgrip pattern 3, shown as 14 in FIG. 2, with the highest pretest AI of 92.55% averaged over 10 subjects, 15 is the least difficult handgrip pattern; and that handgrip pattern 4, shown as 16 in FIG. 2, with the lowest pretest AI of 76.75%, is the most difficult. Further observation reveals that the rank order of difficulty for the six handgrip patterns, in terms of AI scores, was identical from pretest to post-test; this consistency was not observed with the RMS error scores.

Table II documents a statistically significant improvement in joint-position tracking performance, measured with consistency between both scoring methods, in patterns: 1($p<0.05$), 2($p<0.01$), 3($p<0.01$), 5($p<0.05$) and 6($p<0.001$).

The joint-position AI scores suggest that joint-position pattern 6, shown as 40 in FIG. 3, with a pretest AI of 89.02%, is the least difficult; and joint-position pattern 3, shown as 34 in FIG. 3, with a pretest AI of only 66.53%, 30 is the most difficult. The order of difficulty for the six joint-position patterns, ranked by AI scores, is identical from pretest to post-test; but as before, the RMS error scores do not reflect this same consistency.

The tracking maneuvers of this invention, validly resemble the operations of many self-regulating systems of error containment, or servomechanisms, within the body. One such example is standing balance in which sensory feedback is used to pilot fine adjustments of postural motor activity in order to maintain the desired target of vertical stability. Measurement of the accuracy with which one pursues these targets with tracking instrumentation is then merely a quantification of normal, albeit isolated, performance.

Although alternative measures of tracking performance exist, including the measurement of time-on-target and absolute error, RMS error has gained the most favor for the majority of tracking situations. See E. Poulton, Tracking Skill and Manual Control, New York, Academic Press, Inc. (1974); C. Kelley, The Measurements of Tracking Proficiency, 11 Human Factors 43-64 (1969). In this invention, tracking scores are indeed based on the conventional RMS error calculation but, in addition, a second, standardized score is also determined. The resultant AI score proves to be equally reliable with the conventional RMS error score in detecting improved tracking performance from pretest to posttest.

Figure 7A:
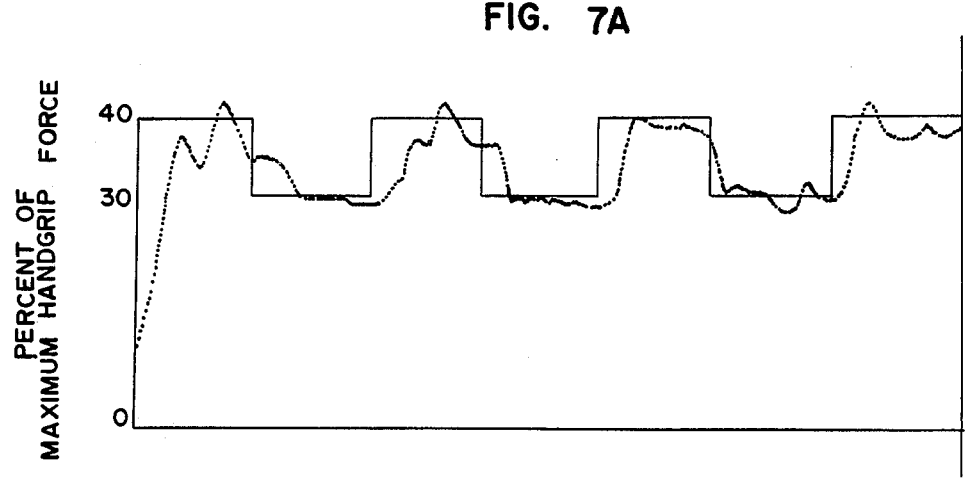
FIG. 7a shows the handgrip tracking performance for handgrip pattern 1 of a test subject with a maximum handgrip force of 64 lbs.
Figure 7B:
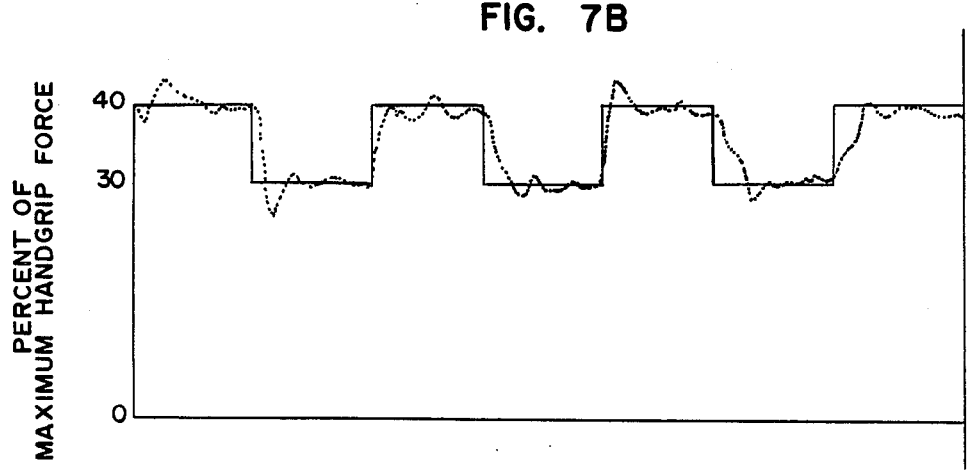
FIG. 7b shows the handgrip tracking performance for handgrip pattern 1 of a test subject with a maximum handgrip force of 166 lbs.

Additionally, the AI scoring method provides a measure of performance that is unconfounded by strength or range of motion differences among individuals. This advantage is shown in FIGS. 7a and 7b. FIGS. 7a and 7b show handgrip pattern 1, shown as 10 in FIG. 2, as a solid line while the subject's tracking performance is shown as a dotted line. FIG. 7a is the performance of an individual with a maximum handgrip force of 64 lbs. and FIG. 7b is the performance of an individual with a maximum handgrip force of 166 lbs. Visual comparison between FIGS. 7a and 7b reveals more accurate tracking in FIG. 7b, but RMS scores, 3.879 lbs. in FIG. 7a and 4.091 lbs. in FIG. 7b, erroneously suggest better tracking performance in FIG. 7a. This contradiction is due to the difference in amplitude scale between the two patterns. Standardization of the scores, the AI value, correctly reflects the more accurate performance in FIGS. 7a and 7b: AI in FIG. 7a is 83.225% and AI in FIG. 7b is 93.153%.

The AI scores hold a further benefit in that they possess a much narrower standard deviation about the mean than the RMS error scores, as revealed in Tables I and II. This narrower range of normal values, determined in various age groups, serves as a more sensitive standard against which patients can be compared for evaluative or diagnostic purposes. Indeed, such normative data already exists for the assessment of strength and range of motion at various muscle groups and joints, but no such standardized values are commonly used for the assessment of motor control.

An important clinical application of this invention is the ability to quantitate change in performance as a result of treatment. The results of the ten individuals, summarized in Tables 1 and 2, show that the tracking system described herein is sensitive enough to detect significant improvement in many of the tracking patterns as a consequence of limited practice. The reason why the performance in some of the patterns did not show significant improvement is not perfectly clear; however, the level of difficulty may play a factor. In the case of handgrip tracking, the three patterns which did not show significant improvement were considered to be the least difficult handgrip patterns based on AI scores. Perhaps the pretest scores in these patterns are near the limit of human performance leaving little freedom for further improvement. However, the performances with the joint-position patterns do not abide by the same proposition, and so the explanation remains inconclusive.

Nevertheless, it is anticipated that disabled individuals receiving treatment to augment motor control would have markedly reduced pretest tracking scores, leaving ample opportunity for improvement. Also, similar tracking instrumentation and methods, with controls established to account for motor learning, could be conducted that would allow for the scrupulous appraisal of the various therapeutic regimens designated to improve motor function in individuals with such problems as spasticity, rigidity, ataxia and apraxia.

TABLE I

Values of t-Test for Change in Handgrip Tracking Scores (RMS and AI) from Pretest to Posttest

| Patteren | N | Scoring Method | Pretest X ± s | Posttest X ± s | Mean Difference | t | p |
|---|---|---|---|---|---|---|---|
| 1 | 10 | RMS (lbs.) | 3.264 ± 0.578 | 3.124 ± 0.952 | −0.140 | −0.46 | 0.327 |
|   |    | AI (%)     | 89.58 ± 2.85  | 90.61 ± 2.11  | 1.04   | 1.39  | 0.10  |
| 2 | 10 | RMS (lbs.) | 2.635 ± 0.819 | 2.254 ± 0.611 | −0.381 | −2.04 | 0.036[a] |
|   |    | AI (%)     | 82.29 ± 4.24  | 85.04 ± 1.95  | 2.75   | 2.18  | 0.029[a] |
| 3 | 10 | RMS (lbs.) | 2.295 ± 0.695 | 2.430 ± 1.10  | 0.135  | 0.40  | 0.652 |
|   |    | AI (%)     | 92.55 ± 2.04  | 92.38 ± 2.56  | −0.17  | −0.21 | 0.580 |
| 4 | 10 | RMS (lbs.) | 3.458 ± 0.968 | 2.573 ± 0.60  | −0.885 | −5.57 | <0.001[c] |
|   |    | AI (%)     | 76.75 ± 4.76  | 82.67 ± 3.37  | 5.91   | 8.61  | <0.001[c] |
| 5 | 10 | RMS (lbs.) | 2.742 ± 1.058 | 2.551 ± 1.399 | −0.192 | −1.25 | 0.122 |
|   |    | AI (%)     | 90.22 ± 2.60  | 91.02 ± 3.05  | 0.80   | 1.74  | 0.058 |
| 6 | 10 | RMS (lbs.) | 1.50 ± 0.494  | 1.212 ± 0.310 | −0.288 | −3.58 | 0.003[b] |
|   |    | AI (%)     | 80.51 ± 4.05  | 84.11 ± 2.91  | 3.59   | 4.24  | 0.001[b] | a = significant at 0.05 level
b = significant at 0.01 level
c = significant at 0.001 level

TABLE II

Values of t-Test for Change in Joint Position Tracking Scores (RMS and AI) from Pretest to Posttest

| Patteren | N | Scoring Method | Pretest X ± s | Posttest X ± s | Mean Difference | t | p |
|---|---|---|---|---|---|---|---|
| 1 | 10 | RMS (degs) | 8.737 ± 1.793  | 6.838 ± 2.225  | −1.898 | −2.37 | 0.021[a] |
|   |    | AI (%)     | 82.58 ± 3.49   | 85.38 ± 3.49   | 2.81   | 2.67  | 0.013[a] |
| 2 | 10 | RMS (degs) | 11.428 ± 3.537 | 7.997 ± 1.962  | −3.431 | −3.35 | 0.005[b] |
|   |    | AI (%)     | 77.28 ± 7.03   | 84.10 ± 3.90   | 6.82   | 3.35  | 0.005[b] |
| 3 | 10 | RMS (degs) | 13.328 ± 2.398 | 11.706 ± 3.109 | −1.623 | −3.79 | 0.002[b] |
|   |    | AI (%)     | 66.53 ± 6.02   | 70.41 ± 8.15   | 3.87   | 3.26  | 0.005[b] |
| 4 | 10 | RMS (degs) | 12.042 ± 2.131 | 11.942 ± 2.971 | −0.100 | −0.13 | 0.448 |
|   |    | AI (%)     | 69.57 ± 5.24   | 71.45 ± 7.52   | 1.88   | 1.10  | 0.149 |
| 5 | 10 | RMS (degs) | 9.764 ± 2.358  | 8.665 ± 2.307  | −1.098 | −2.68 | 0.013[a] |
|   |    | AI (%)     | 76.48 ± 5.68   | 79.13 ± 5.56   | 2.65   | 2.68  | 0.013[a] |
| 6 | 10 | RMS (degs) | 4.723 ± 1.878  | 3.262 ± 1.08   | −1.461 | −4.71 | <0.001[c] |
|   |    | AI (%)     | 89.02 ± 4.37   | 92.42 ± 2.51   | 3.40   | 4.71  | <0.001[c] | a = significant at 0.05 level
b = significant at 0.01 level
c = significant at 0.001 level

I claim:

1. Tracking instrumentation for measuring human motor control comprising:
   digital computer means;
   monitor means for displaying graphics in response to said computer means;
   load cell means for converting a force exerted by one or more muscles into a corresponding proportional electrical signal;
   analog-to-digital convertor means for periodically sampling and converting said electrical signal into a series of digital words, each word representing a force amplitude value at a given moment;
   software means operable in said computer for:
   (a) causing said computer means to generate a predetermined pattern on said monitor;
   (b) receiving said words in real time from said convertor means and scaling said represented force amplitude values according to a predetermined scaling factor for display on said monitor; and
   (c) plotting scaled values on said monitor superimposed on said pattern, said values being plotted according to the moment acquired so that the user may adjust said force in an attempt to track said pattern as said plotted values sweep across said monitor;
   said software means further including means for recording said words and for analyzing the deviation of the corresponding scaled values to determine a normalized accuracy indication value quantifying tracking performance, said analyzing means including means for:
   (a) calculating a first root mean square difference between said pattern and said values representing force amplitude;
   (b) calculating a second root mean square difference between said pattern and a baseline, said baseline corresponding to zero Delete Force level from said load cell means; and
   (c) calculating said normalized accuracy indication values as a function of the ratio between said first root mean square difference and said second root means square difference.

2. Tracking instrumentation for measuring human motor control comprising:
   digital computer means;
   monitor means for displaying graphics in response to said computer means;
   means for converting a position in a range of motion into a corresponding proportional electrical signal;
   analog-to digital convertor means for periodically sampling and converting said electrical signal into a series of digital words, each word representing a position value at a given moment;
   software means operable in said computer for:
   (a) causing said computer means to generate a predetermined pattern on said monitor;
   (b) receiving said words in real time from said convertor means and scaling said represented values according to a predetermined scaling factor for display on said monitor; and (c) plotting scaled on said monitor superimposed on said pattern, said values being plotted according to the moment acquired so that the user may adjust said position in an attempt to track said pattern as said plotted values sweep across said monitor; and said software means further including means for recording said words and for analyzing the deviation of the corresponding scaled values to determine a normalized accuracy indication value quantifying tracking performance, said analyzing means including means for:

(a) calculating a first root mean square difference between said pattern and said represented values;

(b) calculating a second root mean square difference between said pattern and a baseline, said baseline corresponding to a zero level output from said means for converting; and (c) calculating said normalized accuracy indication value as a function of the ratio between said first root mean square difference and said second root mean square difference.

3. The apparatus according to claim 2 wherein said pattern may be selected from a standard library of predetermined patterns.

4. The tracking instrumentation of claim 1 or 2 further wherein said software means includes means operable in said computer to determined said predetermined scaling factor using digital words produced by said analog-to-digital convertor means in response to a maximum force exerted on said load cell means by a user to be tested, said predetermined scaling factor determined so that less than 100% of said maximum force is required to be applied to said load cell means to cause the resulting plotted scaled value to reach the maximum amplitude of said pattern displayed on said monitor.

5. Apparatus according to claims 1, 2, or 3 wherein said pattern is steady-state.

6. A method for obtaining and quantifying tracking performance data obtained from tracking instrumentation for measuring human motor control said performance data corresponding to a tracking pattern against which the performance data is evaluated, said method comprising the steps of:

(a) generating a tracking pattern on a monitor;

(b) generating a tracking element on said monitor;

(c) generating an electrical signal in response to a patient's muscle activity so that said electrical signal can be varied by controlling the muscle activity;

(d) controlling the position of said tracking element on said monitor with said electrical signal;

(e) recording said electrical signal as said patient attempts to track said pattern;

(f) converting said electrical signal to performance data representing tracking;

(g) calculating a first root mean square difference between said pattern and said data representing tracking performance;

(h) calculating a second root mean square difference between said pattern and a baseline, said baseline corresponding to zero level performance data; and (i) calculating a normalized accuracy indication value which is a function of the ratio between said first root mean square difference and said second root mean square difference.

7. The system according to claims 1, 2, or 6 wherein said normalized accuracy indication value is expressed as:

$$AI = 100(1-E/P)$$

wherein AI is said normalized accuracy indication value, E is said first root mean square difference and P is said second root mean square difference.

UNITED STATES PATENT AND TRADEMARK OFFICE
CERTIFICATE OF CORRECTION

PATENT NO. : 4,885,687

DATED : December 5, 1989

INVENTOR(S) : James R. Carey

It is certified that error appears in the above-identified patent and that said Letters Patent is hereby corrected as shown below:

Front page, Col. 1, in the Title, "Trackig" should be --Tracking--.

Col. 5, line 23-24, "electrogoniometer" should be --electrogonimeter--.

Col. 6, line 60, "raning" should be --ranging--.

Col. 7, line 25, after "0.01)" insert --.--.

Col. 9, Tables I and II, "Patteren" should be --Pattern--.

Col. 10, line 47, delete "Delete".

Col. 10, line 47, "Force" should be --force--.

Col. 11, line 3, after "scaled" insert --values--.

Signed and Sealed this

Ninth Day of April, 1991

*Attest:*

HARRY F. MANBECK, JR.

*Attesting Officer*   *Commissioner of Patents and Trademarks*